(12) United States Patent
Erskine

(10) Patent No.: US 8,002,746 B2
(45) Date of Patent: Aug. 23, 2011

(54) WINGED NEEDLE WITH NEEDLE SHIELD

(75) Inventor: Timothy J. Erskine, Sandy, UT (US)

(73) Assignee: Erskine Medical LLC, High Falls, NY (US)

( * ) Notice: Subject to any disclaimer, the term of this patent is extended or adjusted under 35 U.S.C. 154(b) by 391 days.

(21) Appl. No.: 11/817,687

(22) PCT Filed: Mar. 6, 2006

(86) PCT No.: PCT/US2006/007912
§ 371 (c)(1),
(2), (4) Date: Sep. 4, 2007

(87) PCT Pub. No.: WO2006/096636
PCT Pub. Date: Sep. 14, 2006

(65) Prior Publication Data
US 2008/0195055 A1     Aug. 14, 2008

Related U.S. Application Data

(60) Provisional application No. 60/659,226, filed on Mar. 7, 2005, provisional application No. 60/659,217, filed on Mar. 7, 2005, provisional application No. 60/659,213, filed on Mar. 7, 2005, provisional application No. 60/714,954, filed on Sep. 7, 2005.

(51) Int. Cl.
*A61M 5/00* (2006.01)
*A61M 5/32* (2006.01)
(52) U.S. Cl. ...................... 604/110; 604/198
(58) Field of Classification Search .................. 604/110, 604/164.01, 192, 193, 198
See application file for complete search history.

(56) References Cited

U.S. PATENT DOCUMENTS

| | | | |
|---|---|---|---|
| 4,588,398 A | 5/1986 | Daugherty et al. |
| 4,596,563 A | 6/1986 | Pande |
| 4,755,170 A | 7/1988 | Golden |
| 4,762,516 A | 8/1988 | Luther et al. |
| 4,778,453 A | 10/1988 | Lopez |
| 4,790,828 A | 12/1988 | Dombrowski et al. |

(Continued)

FOREIGN PATENT DOCUMENTS

CN          1145813 A          3/1997

(Continued)

OTHER PUBLICATIONS

Erskine, Australian IP Examination Report No. 2 dated Mar. 3, 2010, Reference No. 30355386/MRF/TLG/tzs, Application No. 2006220690, 2 pages.

(Continued)

*Primary Examiner* — Theodore Stigell
*Assistant Examiner* — Bradley Osinski
(74) *Attorney, Agent, or Firm* — Hoffman Warnick LLC

(57) ABSTRACT

A winged needle set is disclosed. The winged needle set has a housing and opposed wings which can be grasped between the fingers for insertion of the needle into a body. The winged needle set has a finned member which is rotatable about the axis of the needle. Rotation of the finned member towards one of the wings actuates a needle shield, which moves along the needle in the distal direction. In one embodiment, the needle shield has includes a blocking object (such as a ball), a biasing spring and a holder for the blocking object.

16 Claims, 10 Drawing Sheets

U.S. PATENT DOCUMENTS

| | | | |
|---|---|---|---|
| 4,832,696 | A | 5/1989 | Luther et al. |
| 4,834,718 | A | 5/1989 | McDonald |
| 4,846,809 | A | 7/1989 | Sims |
| 4,887,998 | A | 12/1989 | Martin et al. |
| 4,927,414 | A | 5/1990 | Kulli |
| 4,929,241 | A | 5/1990 | Kulli |
| 4,931,048 | A | 6/1990 | Lopez |
| 4,944,725 | A | 7/1990 | McDonald |
| 4,952,207 | A | 8/1990 | Lemieux |
| 4,978,344 | A | 12/1990 | Dombrowski et al. |
| 5,049,136 | A | 9/1991 | Johnson |
| 5,059,180 | A | 10/1991 | McLees |
| 5,215,528 | A | 6/1993 | Purdy et al. |
| RE34,416 | E | 10/1993 | Lemieux |
| 5,261,895 | A | 11/1993 | Kablik |
| 5,304,151 | A | 4/1994 | Kuracina |
| 5,322,517 | A | 6/1994 | Sircom et al. |
| 5,328,482 | A | 7/1994 | Sircom et al. |
| 5,334,158 | A | 8/1994 | McLees |
| 5,344,408 | A | 9/1994 | Partika |
| 5,458,658 | A | 10/1995 | Sircom |
| 5,558,651 | A | 9/1996 | Crawford et al. |
| 5,601,536 | A | 2/1997 | Crawford et al. |
| 5,611,781 | A | 3/1997 | Sircom et al. |
| 5,662,610 | A | 9/1997 | Sircom |
| 5,690,619 | A | 11/1997 | Erskine |
| 5,697,907 | A | 12/1997 | Gaba |
| 5,700,250 | A | 12/1997 | Erskine |
| 5,795,339 | A | 8/1998 | Erskine |
| 5,879,337 | A | 3/1999 | Kuracina et al. |
| 6,001,080 | A | 12/1999 | Kuracina et al. |
| 6,221,047 | B1 | 4/2001 | Greene et al. |
| 6,443,929 | B1 | 9/2002 | Kuracina |
| 6,629,959 | B2 | 10/2003 | Kuracina et al. |
| 6,659,984 | B2 * | 12/2003 | Maclean Crawford et al. .......................... 604/263 |
| 6,689,102 | B2 | 2/2004 | Greene |
| 6,695,814 | B2 | 2/2004 | Greene et al. |
| 6,743,186 | B2 * | 6/2004 | Crawford et al. ............. 600/583 |
| 6,860,871 | B2 | 3/2005 | Kuracina et al. |
| 7,144,387 | B2 | 12/2006 | Millerd |
| 7,322,963 | B2 | 1/2008 | Goh |
| 2003/0036731 | A1 | 2/2003 | Wilkinson et al. |
| 2003/0216687 | A1 | 11/2003 | Hwang |
| 2003/0220587 | A1 | 11/2003 | Swenson |
| 2004/0225262 | A1 | 11/2004 | Fathallah et al. |
| 2005/0119627 | A1 | 6/2005 | Crawford |
| 2008/0171986 | A1 | 7/2008 | Baid |

FOREIGN PATENT DOCUMENTS

| | | | |
|---|---|---|---|
| CN | 1547493 | A | 11/2004 |
| DE | 3802353 | A1 | 8/1989 |
| EP | 0749761 | A1 | 12/1996 |
| EP | 0750916 | A2 | 1/1997 |
| EP | 1369142 | B1 | 8/2005 |
| EP | 2016964 | A1 | 1/2009 |
| FR | 2767480 | A1 | 2/1999 |
| JP | 2002330946 | A | 11/2002 |
| JP | 2002539897 | T | 11/2002 |
| TW | M243216 | | 9/2004 |
| WO | 03011381 | A1 | 2/2003 |
| WO | 2006096633 | A1 | 9/2006 |
| WO | 2006096634 | A1 | 9/2006 |
| WO | 2006096635 | A1 | 9/2006 |

OTHER PUBLICATIONS

Erskine, Canadian Application No. 2,599,943, Office Action dated Nov. 20, 2009, 2 pages.
Erskine, Chinese Application No. 200680007590, Office Action dated Aug. 21, 2009, 11 pages.
Erskine, Australian Application No. 2006220691, Notice of Acceptance dated Jun. 9, 2010, 2 pages.
Erskine, Canadian Application No. 2,599,945, Office Action dated Nov. 13, 2009, 2 pages.
Erskine, Chinese Application No. 200680007484, Notification to Grant Patent Right dated Jun. 11, 2010, 4 pages.
Erskine, Australian Application No. 2006220692, Examiners First Report on Patent Application dated Oct. 21, 2008, 2 pages.
Erskine, Canadian Application No. 2,599,955, Office Action dated Mar. 5, 2010, 2 pages.
Erskine, Chinese Application No. 200680007485.0, Office Action dated Jun. 19, 2009, 6 pages.
Erskine, Chinese Application No. 200680007485.0, Notification to Grant Patent Right dated Jun. 4, 2010, 5 pages.
Erskine, Japanese Application No. P2008-500805, Office Action dated Apr. 20, 2010, 4 pages.
Erskine, Malaysia Application No. PI 20071465, Substantive Examination Report dated Apr. 30, 2010, 3 pages.
Patent Cooperation Treaty, PCT/US06/07912, PCT International Preliminary Report on Patentability, dated Sep. 12, 2007, 5 pages.
Patent Cooperation Treaty, PCT/US06/07912, PCT International Search Report and Written Opinion, dated Jun. 26, 2006, 8 pages.
Erskine, Taiwanese Application No. 095107584, Decision to Grant Patent dated Mar. 4, 2009, 5 pages.
Erskine, Australian Application No. 2006220690, Notice of Acceptance dated Jun. 15, 2010, 3 pages.
Erskine, U.S. Appl. No. 11/817,891, Office Communication dated Oct. 19, 2009, 10 pages.
Erskine, Australian Application No. 2006220689, Examiners First Report on Patent Application dated Jan. 15, 2009, 3 pages.
Erskine, Australian Application No. 2006220689, Patent Granted dated Jun. 18, 2010, 3 pages.
Erskine, Canadian Application No. 2,599,938, Office Action dated Feb. 23, 2010, 2 pages.
Erskine, Chinese Application No. 200680007548.2, Office Action dated Sep. 4, 2009, 4 pages.
Erskine, Chinese Application No. 200680007548.2, Notification to Grant Patent Right dated Jun. 12, 2010, 4 pages.
Erskine, Japanese Application No. P2008-500802, Office Action dated Jun. 29, 2010, 6 pages.
Erskine, Malaysia Application No. PI 20071468, Substantive Examination Report dated Apr. 16, 2010, 2 pages.
Patent Cooperation Treaty, PCT/US06/07910, PCT International Preliminary Report on Patentability, dated Jul. 3, 2007, 20 pages.
Patent Cooperation Treaty, PCT/US06/07909, PCT International Search Report and Written Opinion, dated Jun. 26, 2006, 9 pages.
Erskine, Taiwanese Application No. 095107593, Decision to Grant Patent dated Dec. 11, 2009, 5 pages.
Patent Cooperation Treaty, PCT/US09/036197, PCT International Search Report and Written Opinion dated Apr. 28, 2009, 14 pages.
Patent Cooperation Treaty, PCT/US09/038246, PCT International Search Report and Written Opinion dated May 20, 2009, 11 pages.
Erskine, Australian Application No. 2006220690, Examiner's First Report on Patent dated Nov. 11, 2008, 3 pages.
Erskine, Chinese Application No. 200680007590, Office Action dated May 21, 2010, 4 pages.
Erskine, European Application No. EP06737126, Supplementary European Search Report dated Feb. 11, 2010, 4 pages.
Patent Cooperation Treaty, PCT/US06/07910, PCT International Search Report and Written Opinion, dated Jul. 5, 2006, 8 pages.
Erskine, Taiwanese Application No. 095107587, Office Action dated Oct. 12, 2009, 12 pages.
Erskine, Australian Application No. 2006220691, Examiner's First Report on Patent dated Jan. 19, 2009, 2 pages.
Erskine, Chinese Application No. 200680007484, Office Action dated Aug. 21, 2009, 13 pages.
Erskine, Taiwanese Application No. 095107585, Office Action dated Apr. 6, 2009, 9 pages.
Erskine, Taiwanese Application No. 095107585, Office Action dated Oct. 15, 2009, 7 pages.
Erskine, European Application EP06737125, Supplementary European Search Report dated Feb. 10, 2010, 7 pages.
Patent Cooperation Treaty, PCT/US06/07909, PCT International Preliminary Report on Patentability, dated Aug. 16, 2007, 14 pages.
Patent Cooperation Treaty, PCT/US06/07911, PCT International Preliminary Report on Patentability, dated Feb. 12, 2007, 4 pages.
Patent Cooperation Treaty, PCT/US06/07911, PCT International Search Report and Written Opinion, dated Jun. 23, 2006, 8 pages.

Erskine, U.S. Appl. No. 11/817,891, Office Communication dated Jun. 11, 2010, 11 pages.
Erskine, Canadian Application No. 2,599,943, Office Action dated Dec. 30, 2010, 2 pages.
Erskine, Canadian Application No. 2,599,945, Notice of Allowance dated Nov. 25, 2010, 1 pages.
Erskine, Canadian Application No. 2,599,955, Office Action dated Dec. 21, 2010, 3 pages.
Erskine, Canadian Application No. 2,599,938, Office Action dated Dec. 20, 2010, 2 pages.
Erskine, Japanese Application No. P2008-500805, Final Office Action dated Jan. 25, 2011, 25 pages.
Erskine, Japanese Application No. P2008-500804, Notice to Grant dated Feb. 2, 2011, 6 pages.
Erskine, Mexican Application No. MX/a/2007/010944, Office Action dated Mar. 11, 2011, 4 pages.
Erskine, Japanese Application No. JP07-5616-XY, Decision to Grant a Patent, dated Apr. 5, 2011, 6 pages.
Erskine, Taiwan Application No. 095107585, Office Action, dated Mar. 17, 2011, 3 pages.
Erskine, Mexian Application No. MX/a/2007/010946, Office Action, dated Apr. 2011, 2 pages.
Erskine, Japan Application No. P2008-500802, Notice of Reasons for Rejection, dated Apr. 5, 2011, 4 pages.
Erskine, U.S. Appl. No. 11/817,892, Office Action, dated Apr. 28, 2011, 25 pages.
Erskine, China Application No. 201010109122.6, Office Action, dated Apr. 1, 2011, 11 pages.

* cited by examiner

WINGED NEEDLE WITH NEEDLE SHIELD

CROSS-REFERENCE TO RELATED APPLICATIONS

This patent application claims priority from, and expressly incorporates by reference, the following provisional patent applications:

- 60/659,226—Shielding Apparatus for Locking onto a Needle—filed on Mar. 7, 2005;
- 60/659,217—Needle Shielding Apparatus with Tubular Needle Cover—filed on Mar. 7, 2005;
- 60/659,213—Needle Shielding Apparatus with Tether to Needle Hub—filed on Mar. 7, 2005;
- 60/714,954—Blood Collection Device with Needle Shield—filed on Sep. 7, 2005.

BACKGROUND

This patent application describes and relates to medical devices for collecting blood or other bodily fluids or infusing fluids, such devices using needles to pierce a human or animal body. It includes a device for shielding such needles.

SUMMARY OF THE INVENTION

An embodiment of the invention is a winged needle set which has a housing with at least one outwardly extending wing (preferably two). A finned member is secured to the housing. The finned member is oriented generally radially outward relative to the longitudinal axis of the needle and is rotatable relative to the housing from a first non-shielding position to a second shielding position. A needle shield assembly is mounted relative to the housing such that the needle shield assembly is slidable longitudinally along the needle. When the finned member is rotated from the first non-shielding position to the second shielding position, the needle shield assembly is unlocked by a release mechanism and permitted to slide relative to the housing along the needle shaft, shielding the needle. In the first non-shielding position, the finned member is oriented from approximately vertical to approximately 60 degrees from vertical. The wing is moveable and can be brought towards the finned member (or rotated or folded) when the finned member is in the first non-shielding position. A spring biases the needle shield assembly to the second shielding position. The wings may be rotatable relative to the housing such that the wings can be brought towards the finned member when the finned member is in the first non-shielding position.

DETAILED DESCRIPTION

Figure 1:
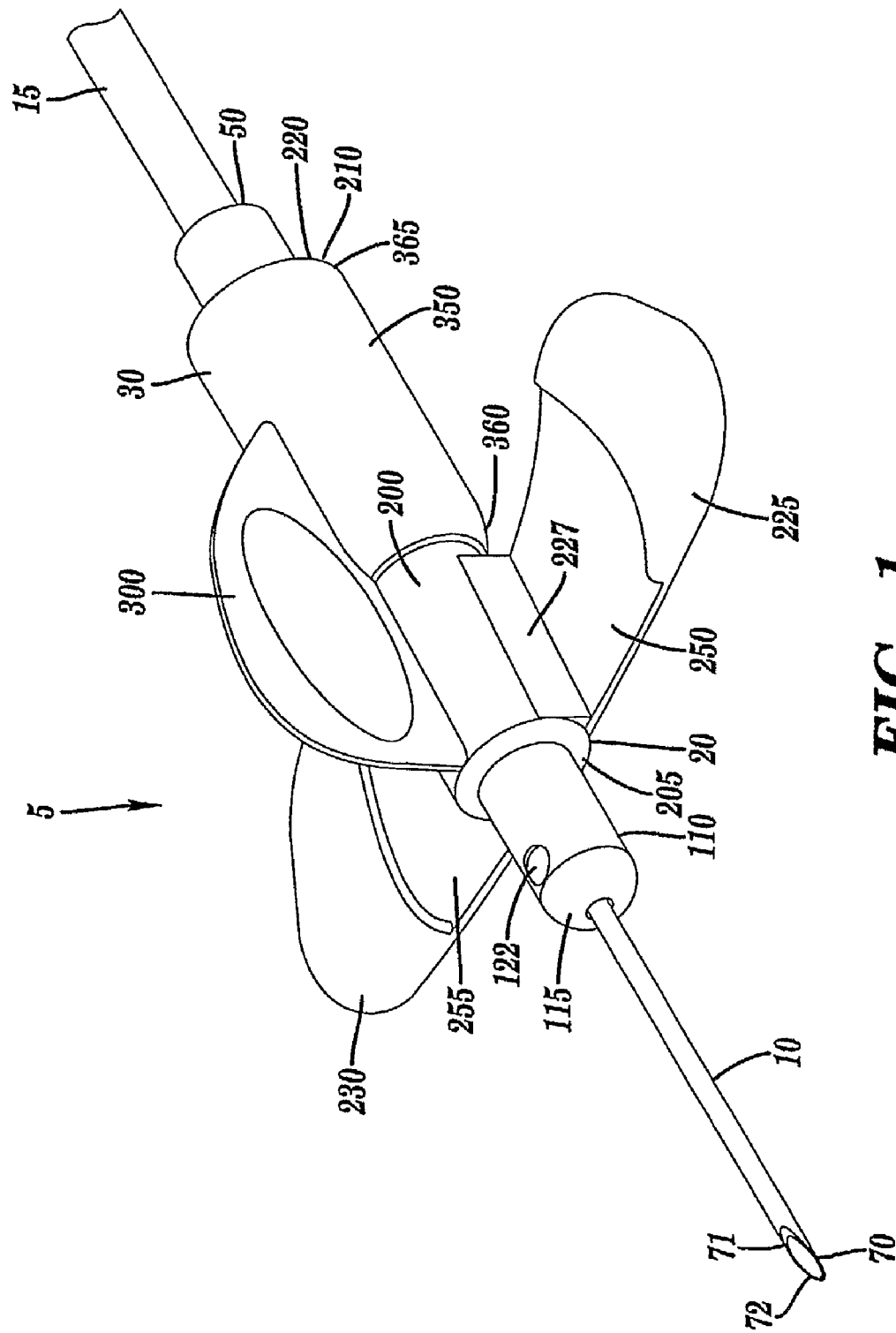
FIG. 1 is an isometric view of a device incorporating the invention before deployment of the needle shield.

The following is a description of the preferred embodiment of the invention as applied to a blood collection device. A similar structure may be used for infusing fluids. The purpose of the blood collection device 5 is to pierce a blood vessel (or other organ) using needle 10 and remove blood (or other fluid) to a receptacle via tube 15. This device makes use of technology described in U.S. Provisional Patent Application No's 60/659,213, 60/659,217 and 60/659,226 which are incorporated herein by reference.

The preferred embodiment of the device is made up of the following basic components:

Housing 20, with wings 225 and 230.
Needle 10, secured to needle hub 50 and in fluid communication with tube 15.
Needle shield assembly 110.
Actuator assembly 30, with rotatable fin 300.

Housing 20 has a generally cylindrical body 200, having distal end 205 and proximal end 210. Distal end 205 has an opening 215. Proximal end 210 has an opening 220. A passageway 236 extends between the openings in the proximal and distal ends. Passageway 236 is dimensioned such that shield assembly 110 fits axially in it, and such that shield assembly 110 can slide axially along it. Housing 20 is provided with wings 225 and 230, which can bend upwards towards each other and towards fin 300 on actuator assembly 30. Fillet 227 facilitates molding of wings 225 and 230 and housing 20. An identical fillet is provided to stabilize wing 230. Wings 225 and 230 are provided with indentations 250 and 255 respectively. These are shaped and dimensioned to accommodate fin 300. Housing body 200 is provided with a slot 260, designed to accommodated key 190 on shield assembly 110 (described below). Slot 260 extends from proximal end 210 (where it is open) towards distal end 205 of housing body 200, where it is closed. Slot 260 has a proximal end 265 and a distal end 270.

Figure 6:
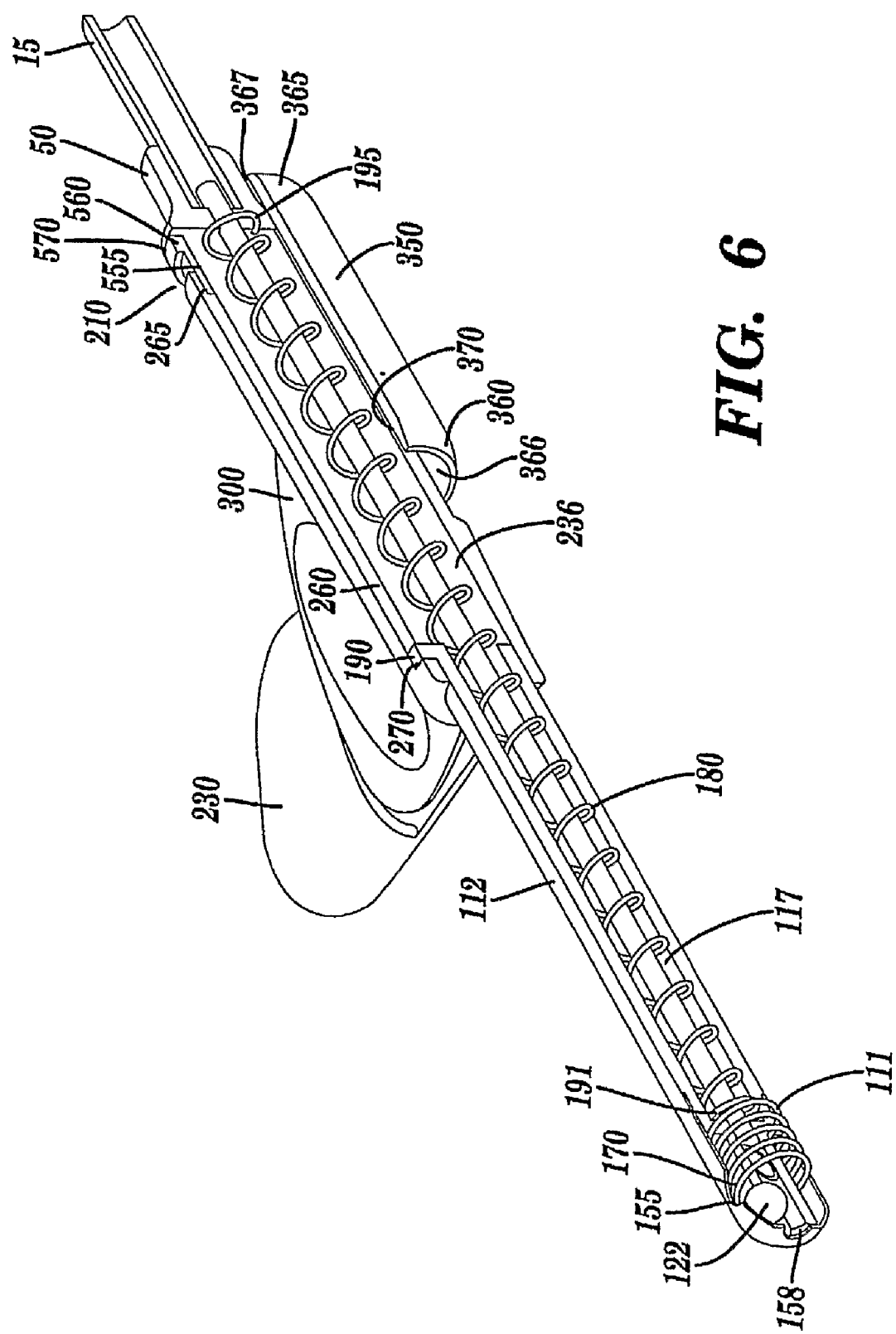
FIG. 6 is a cross-sectional isometric view of a device incorporating the invention after deployment of the needle shield.
Figure 7:
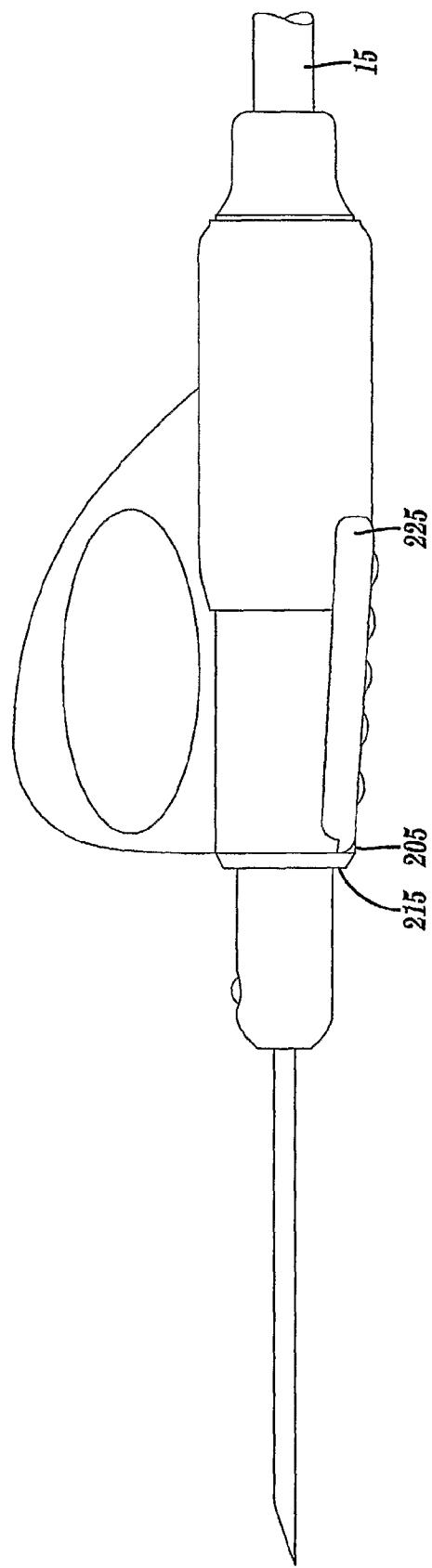
FIG. 7 is a side view of a device incorporating the invention before deployment of the needle shield.
Figure 8:
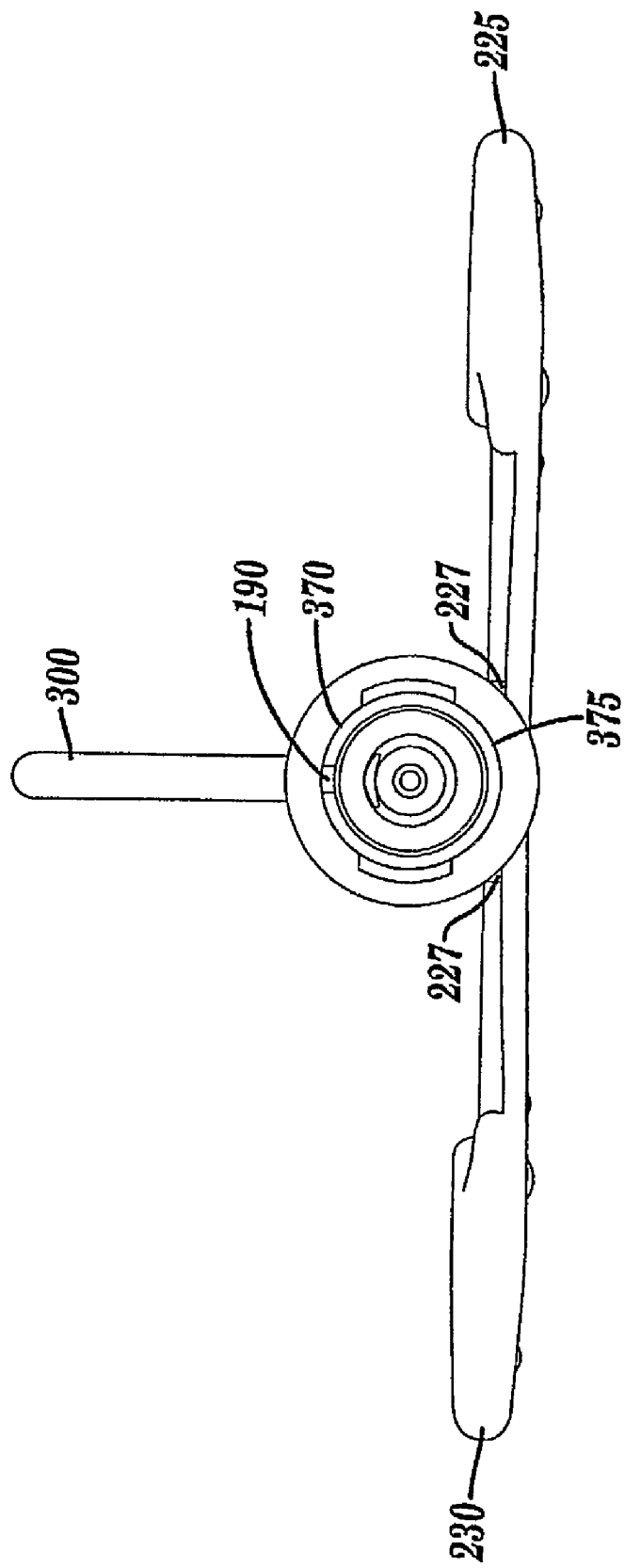
FIG. 8 is a cross sectional view through section A-A in FIG. 7.

Needle hub 50 has a stepped distal end 550 forming a hollow open ended cylinder 555 which mates with opening 215 in proximal end 210 of housing body 200. The step forms a flange 570. Stepped proximal end 550 is provided with a slot 560 (see FIG. 6), which aligns with slot 260 and extends from flange 570, along cylinder 555 to its open end. Slot 560 also accommodates key 190. Slot 560 is open at the front to allow key 190 to move in it and closed at the back to prevent key 190 from leaving it.

Proximal end 75 of needle 10 is glued into needle hub 50. Rear end 565 is an open ended cylinder extending proximally which is designed to mate with tube 15, thus permitting fluid to flow through needle 10 and tube 15 and into a receptacle for collection.

Figure 2:
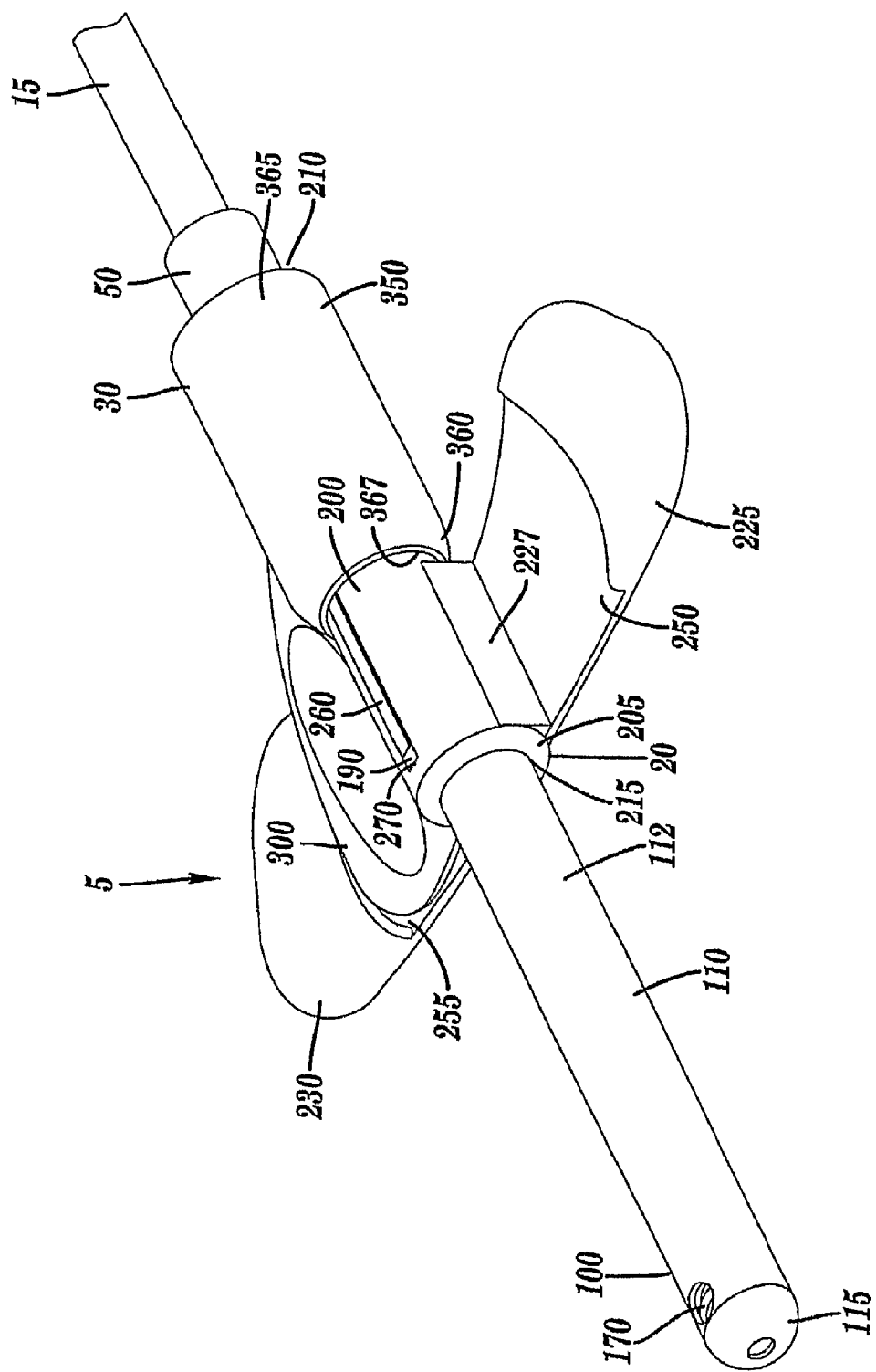
FIG. 2 is an isometric view of a device incorporating the invention after deployment of the needle shield.
Figure 3:
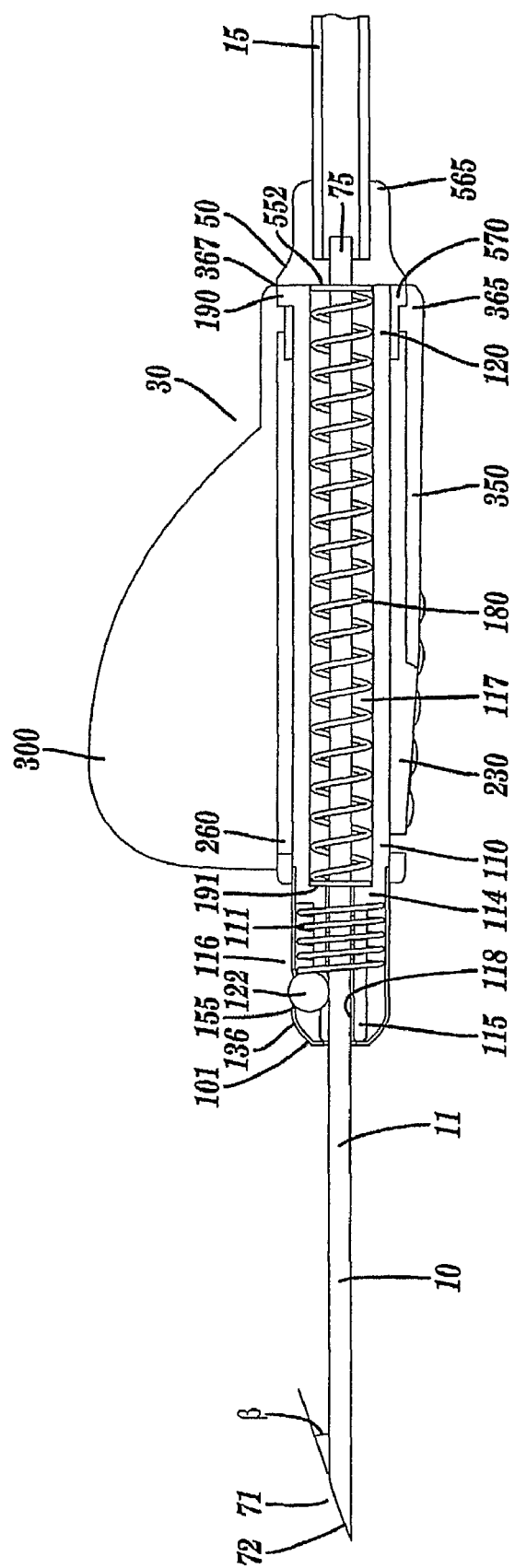
FIG. 3 is a cross-sectional side view of a device incorporating the invention before deployment of the needle shield.
Figure 4:
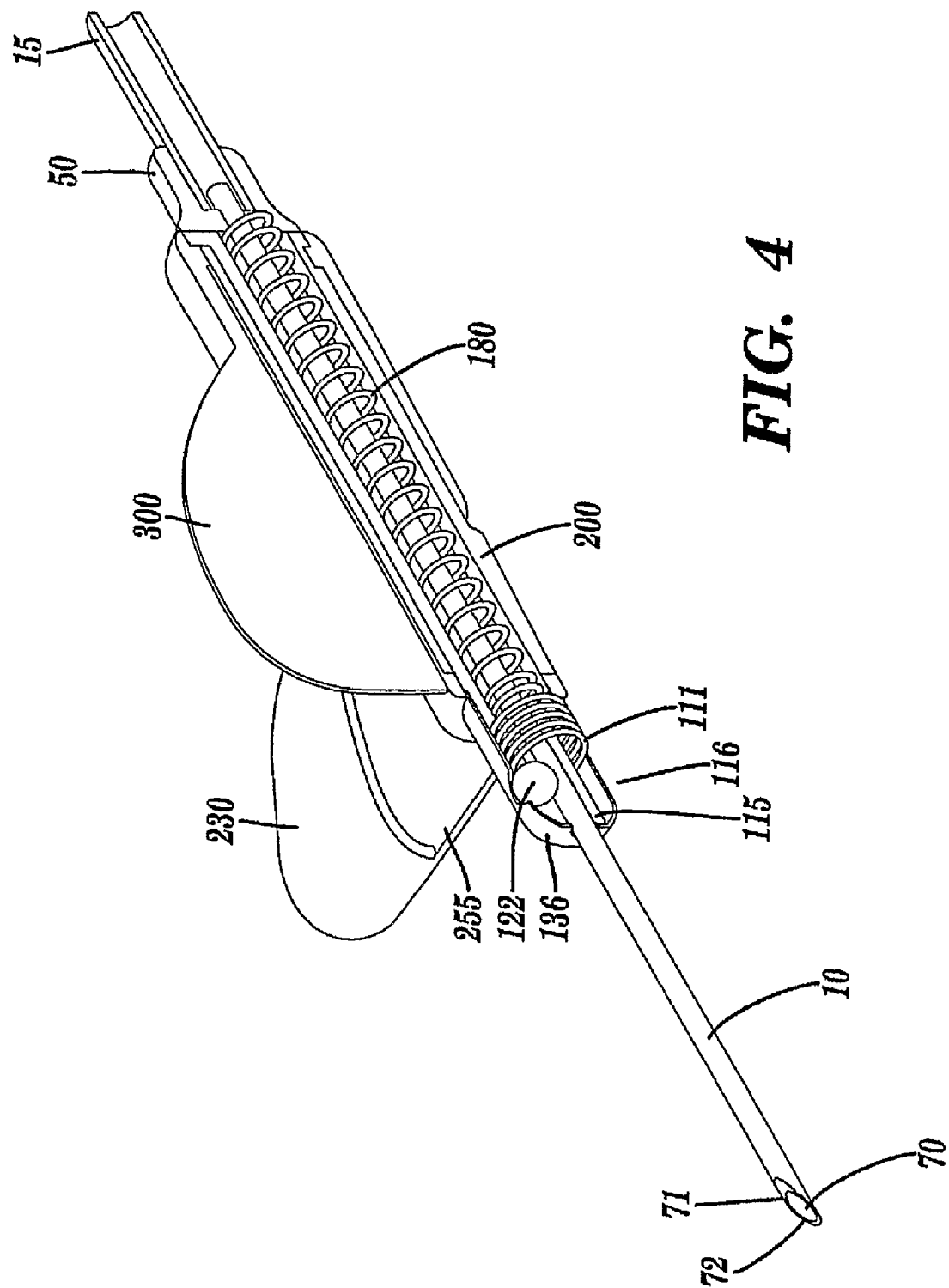
FIG. 4 is a cross-sectional isometric view of a device incorporating the invention before deployment of the needle shield.
Figure 5:
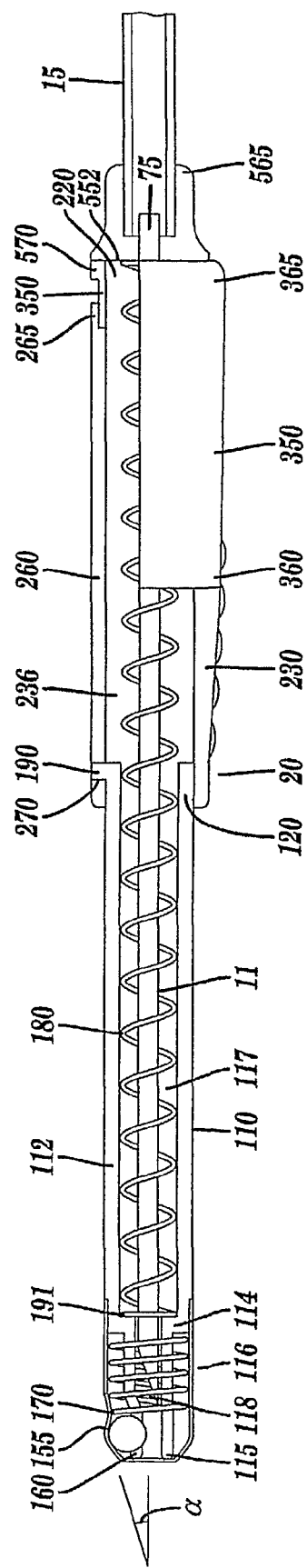
FIG. 5 is a cross-sectional side view of a device incorporating the invention after deployment of the needle shield.
Figure 9:
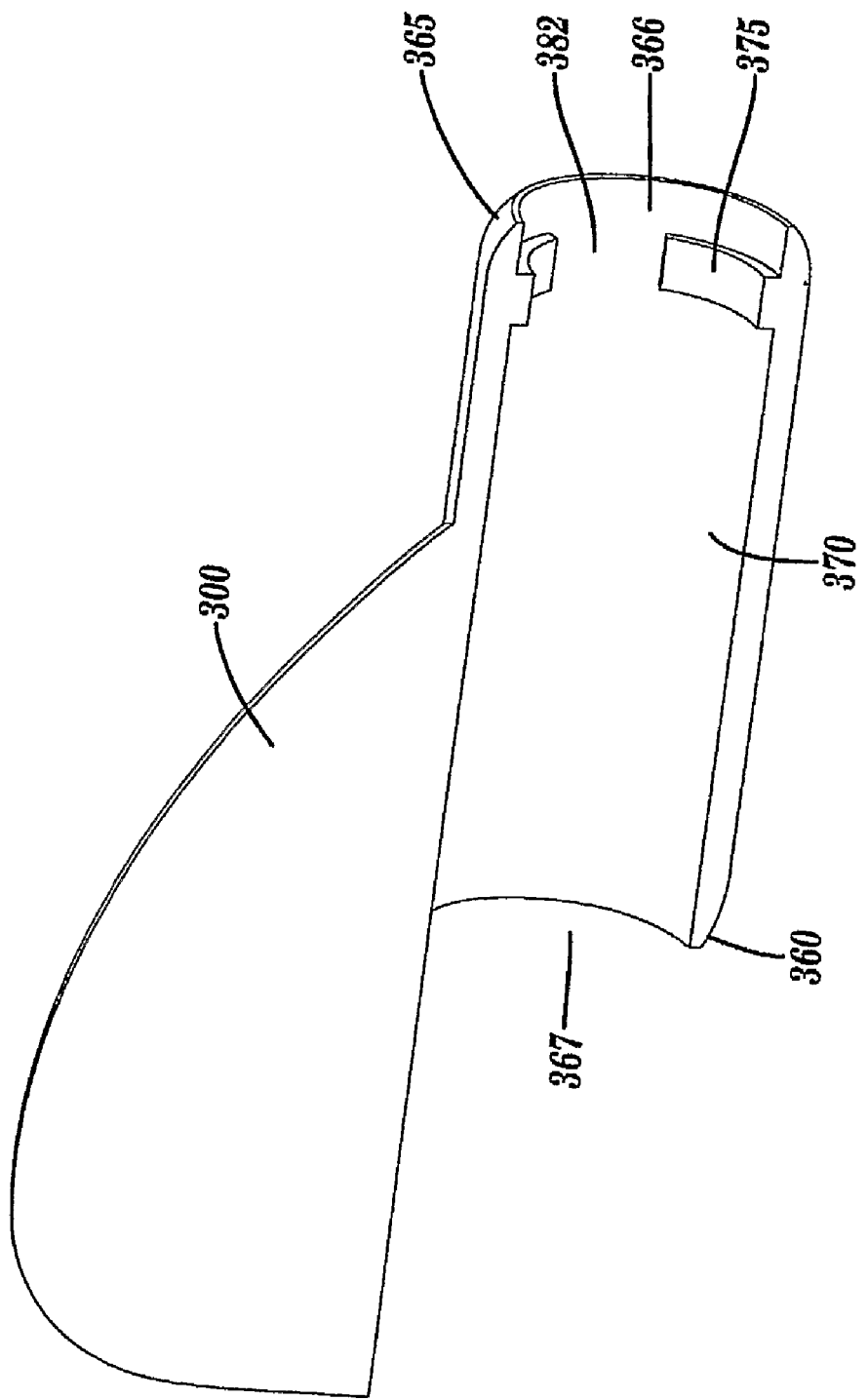
FIG. 9 is an isometric view of part of the needle shield actuator of a device incorporating the invention.

Fin assembly 30 has a cylindrical body section 350 having a proximal end 365 and a distal end 360. Proximal and distal ends 365, 360 are respectively provided with openings 366 and 367. A passage 370 extends between the proximal and distal ends. Passage 370 has an inner surface 372. Fin assembly 30 fits concentrically over cylindrical body 200 and can rotate about the axis of cylindrical body 200, constrained by wings 225 and 230. Near proximal end 365, inner surface 372 is provided with a circumferential rim 375. Rim 375 has sections removed from it forming openings 380 and 382 (only 382 is shown in FIG. 9, 380 being substantially identical to 382), dimensioned to allow passage of key 190. These openings start at about +70 degrees and −70 degrees to the vertical and describe arcs of about 30 degrees. When fin assembly 30 is in a first, non-shielding position (see, FIGS. 1, 3, 4, 7, and 8), rim 375 blocks key 190. In that first position, when key 190 is blocked by rim 375, fin 300 is vertical. When fin 300 is rotated clockwise or counter-clockwise, cylindrical body section 350 (and hence rim 375) rotates about the axis of body section 200. When fin assembly 30 is rotated to a second, shielding position (anywhere from about 60 degrees to the vertical to about 90 degrees to the vertical, clockwise or counter-clockwise, see FIGS. 2, 5, and 6) in which key 190 aligns with opening 380 or 382 (depending on the direction of rotation) key 190 is free to travel distally in slot 260. When that happens, under the influence of coil spring 180 abutting inner wall 114 of cylindrical body 112, needle shield assembly 110 will move in the distal direction, thus shielding the needle.

The combination of rim 375 and key 190 thus forms part of a triggering mechanism which allows shield assembly to be unlocked and to move in the distal direction when needle 10 is to be shielded.

When fin 300 has been rotated to a position against either wing 225 or wing 230, fin 300 may be secured to the skin of the patient. To that end, fin 300 may be provided with an adhesive strip. Needle shield assembly 110 has a cylindrical body 112 having a proximal end 120 and distal end 115. Lumen 117 extends between proximal end 120 and distal end 115 and is dimensioned to accommodate needle 10 axially such that it can slide over needle 10. Needle shield assembly 110 fits axially into housing body 200 such that it can slide axially along passageway 236. Proximal end 120 is provided with key 190. As described above, key 190 fits into slot 260 and slot 560. Key 190 prevents shield assembly 110 from rotating relative to housing body 200. It also prevents shield assembly 110 from exiting opening 220 of housing body 200 in the proximal direction, when it abuts distal end 270 of slot 260.

Figure 10:
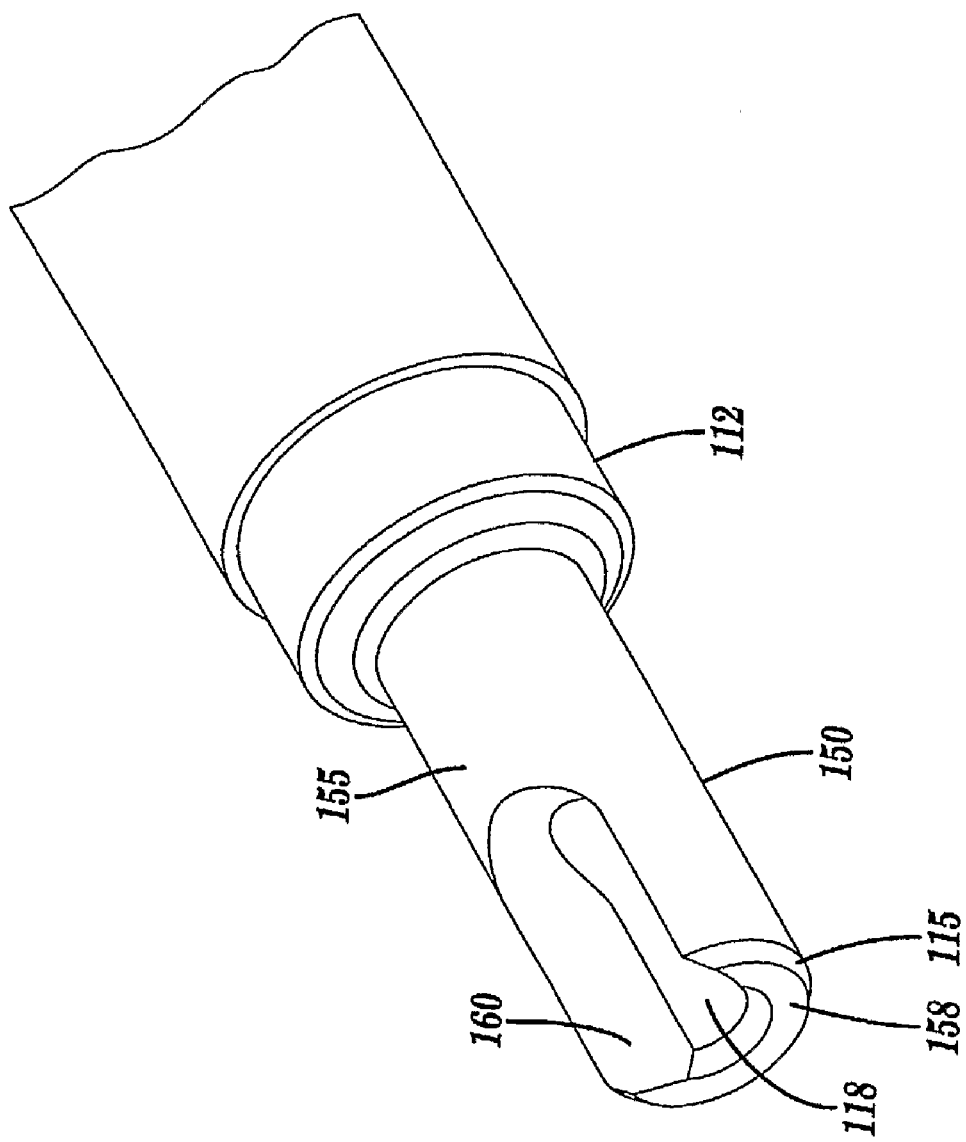
FIG. 10 is an isometric view of the distal end of part of a needle shield used in a device incorporating the invention.

At distal end 115 of needle shield assembly 110 there is a stop mechanism 116 for preventing shield assembly from sliding backwards once needle 70 is shielded. Distal end 115 has a stepped section 150, i.e. a region of reduced diameter in comparison with the remaining cylindrical part of cylindrical body 112. Lumen 117 also has a reduced diameter in stepped section 150 compared with the diameter of lumen 117. In this region, lumen 117 is referred to as lumen 118. The diameter of lumen 118 is only slightly larger than the outer diameter of needle 10. Coil spring 111 is threaded over stepped section 150. The rear end of coil spring 111 abuts the wall 114 formed at the intersection of stepped section 150 and the remainder of cylindrical body 112. Coil spring 111 is a compression spring which exerts its force axially in the proximal and distal directions. Stepped section 150 is also provided with opening 160 in the form of a specially shaped slot extending in a distal direction approximately from the mid point of stepped section 150 to distal end 115 of cylindrical body 112 (see FIG. 10). This opening 160 is dimensioned and shaped such that ball 122 rests in it, with part of ball 122 extending into lumen 118 of cylindrical body 112 and abutting outer surface 11 of needle 10. The force in coil spring 111 keeps ball 122 pressed against needle 10. Shield assembly 110 can thus slide along needle 10 with very low frictional force. Opening 160 is also dimensioned and shaped such that when ball 122 no longer abuts needle 10 (i.e. the tip has passed ball 122), ball 122 can move distally towards distal end of 115 of cylindrical body 112 and radially further into lumen 118, thus blocking axial movement of needle 10 in the distal direction. This is described in greater detail below.

Cap 100 is a metal stamping, dimensioned to fit over stepped section 150, thus enclosing coil spring 111. Cap 100 is provided with opening 170, dimensioned such that part of ball 122 can fit into it, when needle 10 abuts ball 122, but such that ball 122 cannot escape through it. Cap 100 may be limited in size to fit over distal end 115 of cylindrical body 110 or it can extend along the entire length of cylindrical body 115 as a unitary sheath.

Behind stepped section 150, within lumen 117 of cylindrical body 112 lies coil spring 180. Coil spring 180 is a compression spring whose force is exerted axially in the proximal and distal directions. Distal end 191 of coil spring 180 abuts the back of inner wall 114 just behind stepped section 150. Proximal end 195 of coil spring 180 abuts proximal face 552 of needle hub 50 (i.e. in the region of flange 570, but inside cylinder 555. Coil spring 180 is therefore trapped within cylindrical body 112 of shield assembly 110 and inside housing 20. When shield assembly 110 is in its un-actuated position, coil spring 180 is compressed.

The operation of stop mechanism 116 will now be described. Needle tip 70 has a beveled tip with two bevels, first bevel 71 and second bevel 72. When needle shield assembly 110 slides along the length of needle 10 in the distal direction, ball 122 aligns with bevel 71. When ball 122 encounters bevel 71, it is less radially constrained by needle 10 and it moves radially towards the axis of needle 10 under the influence of the force in coil spring 111. Ball 122 thus moves out of opening 170 in cap 100 and radially inwards, further into lumen 118. Ball 122 pivots about edge 155 in opening 170 and slides distally along the length of opening 160. When second bevel is aligned with ball 122, it moves as far as it can in opening 160 and is positioned directly above second bevel 72. At that point it will have traveled as far into lumen 117 as it can, constrained by the dimensions of opening 160 and by distal end 101 of cap 100. Spring 111 has expanded and now constrains ball 122 radially. Ball 122 partially occludes lumen 118, thus blocking the passage of needle tip 70 and preventing shield assembly 110 from being pulled back to expose needle tip 70.

At this point, key 190 has reached distal end 270 of slot 260, so further distal movement of shield assembly 110 relative to needle 10 is prevented. The distance from key 190 to needle tip 70 is set so that when tip 70 is aligned with ball 122, there is sufficient space for ball 122 to move beneath cap 100 in opening 160. Upper surface 136 of distal end 101 of cap 100 (i.e. the part of the needle shield assembly 110 that is immediately radially outward of ball 122 and which ball 122 abuts when the shield is deployed) forms an angle α tangential to ball 122 when ball 122 is moving into its position at least partially occluding lumen 118. This can be seen in FIG. 5. This angle α is set at a value less than the smallest bevel angle β of needle tip 70 (bevel 72 in this case). In the described embodiment, the angle α between the upper surface 136 of distal end 101 and ball 122 is about zero degrees. If that angle is made too large relative to angle β, ball 122 will not be trapped. Distal end 158 of stepped area 155 and cap 100 are dimensioned to overhang so that tip 70 can never emerge from shield assembly 110. It is possible to employ multiple balls sitting in multiple openings the same as opening 160 and 170. If this is done, the overhang can be reduced.

After deployment, but before needle 10 moves distally, part of ball 122 lies in lumen 118 and part of it is urged against the inside of distal end 101 of cap 100 by spring 111. The top of ball 122 lies beneath upper surface 136 of distal end 101 of cap 100. In an alternative embodiment, spring 111, having expanded, closes off the opening 170. If needle 10 moves distally, it will abut ball 122, which will be forced against the inside of end 101 of cap 100. Further distal movement of needle 10 and hence emergence of needle tip 70 from shield assembly 110 will be prevented.

Lumen 118 is sized such that needle 10 fits in it snugly. Thus when needle 10 is moved distally (i.e. shield assembly 110 is moved proximally) and ball 122 abuts needle tip 70, needle 10 will not move away from ball 122. Lumen 170 thus provides support opposite ball 122 to prevent needle 10 from wiggling, and to prevent tip 70 from moving such that it pierces the wall of lumen 118.

In an alternative embodiment, ball 122 fully enters lumen 118. Ball 122 thus has a diameter slightly larger than that of lumen 118. Ball 122 is then axially constrained by lumen 118 and needle 10. In this case, lumen 118 is also dimensioned to provide support for needle 10 opposite ball 122, thus preventing wiggle of the needle and preventing tip 70 from piercing the wall of lumen 118.

Ball 122 moves a distance at least equal to the amount by which it protrudes from opening 155 in cap 100. When the shield is deployed, ball 122 extends into lumen 118 by an amount approximately equal to that distance. This leaves part of lumen 118 un-occluded. If a small gauge needle is used a larger ball is needed in order to occlude lumen 118 sufficiently to prevent tip 70 from poking through the un-occluded part of lumen 118 and so that ball 122 will extend from the surface of needle 10 into opening 160. The same effect can be obtained by making cap 100 smaller and using the same sized ball. If a large gauge needle is used (i.e. a needle having large diameter), the ball can be smaller.

Device 5 is assembled in the following way:

1. Needle shield assembly 110 is dropped into housing 20 from proximal end 210 of housing 20. Key 190 is aligned with slot 260 of housing 20.

2. Finned member 30 is slid over housing 20, from proximal end 210 of housing 20. During this step, fin 300 is at about 60-90 degrees to the vertical, thus aligning opening 380 or opening 382 with key 190. Finned member 30 is then rotated to the vertical position, locking key 190 behind rim 375.

3. Spring 180 is placed inside lumen 117 of shield assembly 110, also from proximal end 210 of housing 20. Distal end 190 of spring 180 abuts the back of wall 114 of needle shield.

4. Needle hub 50 is snapped or glued onto proximal end 210 of housing 20, compressing spring 180. Slot 570 in cylindrical wall of hub 50 is aligned with slot 260 on housing 20.

5. Needle 10 is threaded into hole 113 of needle shield assembly 110, through lumens 118, 117 and spring 180 and glued into needle hub 55.

6. Tube 15 is glued into proximal end 555 of needle hub 55.

The device is used in the following way:

The user grasps wings 225 and 230 between his or her fingertips and brings them together so that they touch fin 300. Alternatively, the device can be held simply by grasping fin 300 between the finger tips. Finger grips are provided in fin 300 for that purpose. Holding the device in either of those two ways, with fin 300 in the vertical (first) position, the user pierces the patient's skin and blood vessel with needle tip 70. Once the blood vessel has been pierced and blood can flow through needle 10, the user rotates fin 300 down towards either wing 225 or 230, thus unblocking key 190 (the second position). Needle shield assembly 110 is thus free to slide axially over the needle in the distal direction, urged by spring 180. Fin 300 is placed in cutout 250 or 255, so it is flush with the relevant wing. Wings 225 and 230 and fin 300 can be taped to the patient's skin while the blood is collected.

In this blood collection (second) position, needle shield assembly 110 has slid axially in the distal direction due to the force of spring 180. Distal end 115 of needle shield assembly lies against the patient's skin. As needle tip 70 is withdrawn, distal end 115 of needle shield assembly, still under the influence of spring 180, moves in the distal direction until, as tip 70 is removed from the patient, it is completely shielded.

The shielding mechanism at the tip of the needle prevents needle shield assembly 110 from sliding in the proximal direction and re-exposing needle tip 70. Key 190 abuts distal end 270 of slot 260, thus preventing distal movement of needle shield assembly 110. Needle 10 is thus completely shielded. Even if fin 300 is rotated back into the first position (to facilitate removal of needle 10 from the patient), shield assembly 110 cannot be retracted because it is blocked from proximal movement by ball 122. Key 190 has moved distally with respect to circumferential rim 375.

Although limited embodiments of the winged needle assemblies, their components, and their applications on different needle devices have been specifically described and illustrated, the descriptions are not intended to limit the scope of the basic invention. Many modifications and variations will be apparent to those skilled in the art. Accordingly, it is to be understood that the winged needle assemblies and their components constructed according to principles of this invention may be embodied other than as specifically described herein. The invention is also defined in the following claims.

I claim:

1. A medical needle assembly comprising:
a needle comprising a longitudinal axis, a proximal end, a sharp distal end and an outer surface;
a housing with a pair of radially outwardly extending wings lying opposite one another defining a plane;
an actuator member concentrically mounted on the housing, and extending substantially radially outwardly from the housing and substantially perpendicular to the longitudinal axis of the needle,
  wherein the actuator member is freely circumferentially rotatable relative to the housing, the pair of radially outwardly extending wings, and the longitudinal axis of the needle between the pair of radially outwardly extending wings, from a first, non-shielding perpendicular to the plane position to a second, shielding position substantially parallel to the plane,
  wherein the actuator member remains substantially perpendicular to the longitudinal axis of the needle;
a needle shield assembly mounted relative to the housing, such that the needle shield assembly is slidable longitudinally along the needle relative to the housing, the pair of radially outwardly extending wings, and the actuator member; and
a release mechanism associated with the actuator member and the needle shield assembly such that when the actuator member is circumferentially rotated relative to the housing, the pair of radially outwardly extending wings, and the longitudinal axis of the needle, from the first, non-shielding position to the second, shielding position, the needle shield assembly is unlocked and permitted to slide relative to the housing, the pair of radially outwardly extending wings, and the longitudinal axis of the needle, along the needle shaft, thereby shielding the needle.

2. The needle assembly of claim 1, wherein, in the first non-shielding position, the actuator member has an orientation from approximately vertical to approximately 60 degrees from vertical.

3. The needle assembly of claim 1, wherein the pair of wings are circumferentially moveable relative to the longitudinal axis of the needle such that each of the pair of wings can be brought towards the actuator member when the actuator member is in the first non-shielding position.

4. The needle assembly of claim 3, wherein the wings can be rotated towards the actuator member.

5. The needle assembly of claim 3, wherein the wings can be folded towards the actuator member.

6. The needle assembly of claim 1, further comprising a spring biasing the needle shield assembly to the second, shielding position, such that when the actuator member is rotated to the second, shielding position, the needle shield moves over the needle.

7. The needle assembly of claim 1, wherein the wings are rotatable relative to the housing such that the wings can be brought towards the actuator member when the actuator member is in the first, non-shielding position.

8. The needle assembly of claim 1, wherein the release mechanism further comprises:
   a key provided on a proximal end of the needle shield assembly; and
   a slot provided in the housing, wherein the slot is shaped and dimensioned to accommodate the key,
   wherein in the first, non-shielding position, the actuator member is oriented vertically relative to the pair of radially outwardly extending wings, and the key is blocked by a portion of the actuator member; and
   wherein in the second, shielding position, the actuator member is circumferentially rotated relative to the housing, the pair of radially outwardly extending wings, and the longitudinal axis of the needle such that it is positioned between about 60 degrees from vertical and about 90 degrees from vertical, and the key aligns with the slot.

9. The needle assembly of claim 8, wherein the portion of the actuator member further comprises a rim located on a proximal end of the actuator member, wherein the rim includes at least one opening;
   wherein in the second, shielding position, the at least one opening is aligned with the slot and the key, and the key is free to travel in a distal direction in the slot.

10. The needle assembly of claim 9, further comprising a spring biasing the needle shield assembly in the distal direction, such that when the actuator member is rotated to the second, shielding position, the key travels in a distal direction in the slot, and the needle shield moves over the needle.

11. The needle assembly of claim 1, wherein the actuator member further comprises a fin, and wherein the fin includes an adhesive for securing the fin to a skin surface of a patient when the actuator member is in the second, shielding position.

12. A medical needle assembly comprising:
   a needle comprising a longitudinal axis, a proximal end, a sharp distal end and an outer surface;
   a housing with a pair of wings extending radially outwardly opposite each other to define a plane;
   an actuator member concentrically mounted on the housing, and extending substantially radially outwardly from the housing and substantially perpendicular to the longitudinal axis of the needle,
      wherein the actuator member is freely circumferentially rotatable relative to the housing, the pair of wings, and the longitudinal axis of the needle, from a first, non-shielding position perpendicular to the plane to a second, shielding position, and
      wherein the actuator member remains substantially perpendicular to the longitudinal axis of the needle;
   a needle shield assembly mounted relative to the housing, such that the needle shield assembly is slidable longitudinally along the needle relative to the housing, the pair of wings, and the actuator member, the needle shield assembly comprising a unitary sheath; and
   a release mechanism associated with the actuator member and the needle shield assembly such that when the actuator member is circumferentially rotated relative to the housing, the pair of wings, and the longitudinal axis of the needle, from the first, non-shielding position to the second, shielding position substantially parallel to the plane, the needle shield assembly is unlocked and permitted to slide relative to the housing, the pair of wings, and the actuator member along the needle shaft, thereby shielding the needle.

13. The needle assembly of claim 12, wherein the release mechanism further comprises:
   a key provided on a proximal end of the needle shield assembly; and
   a slot provided in the housing, wherein the slot is shaped and dimensioned to accommodate the key,
   wherein in the first, non-shielding position, the actuator member is oriented vertically relative to the pair of radially outwardly extending wings, and the key is blocked by a portion of the actuator member; and
   wherein in the second, shielding position, the actuator member is circumferentially rotated relative to the housing, the pair of radially outwardly extending wings, and the longitudinal axis of the needle such that it is positioned between about 60 degrees from vertical and about 90 degrees from vertical, and the key aligns with the slot.

14. The needle assembly of claim 13, wherein the portion of the actuator member further comprises a rim located on a proximal end of the actuator member, wherein the rim includes at least one opening;
   wherein in the second, shielding position, the at least one opening is aligned with the slot and the key, and the key is free to travel in a distal direction in the slot.

15. The needle assembly of claim 14, further comprising a spring biasing the needle shield assembly in the distal direction, such that when the actuator member is rotated to the second, shielding position, the key travels in a distal direction in the slot, and the needle shield moves over the needle.

16. The needle assembly of claim 12, wherein the actuator member further comprises a fin, and wherein the fin includes an adhesive for securing the fin to a skin surface of a patient when the actuator member is in the second, shielding position.

* * * * *